United States Patent
Monstadt et al.

(10) Patent No.: US 7,238,194 B2
(45) Date of Patent: Jul. 3, 2007

(54) DEVICE FOR IMPLANTING OCCLUSION SPIRALS

(75) Inventors: Hermann Monstadt, Bochum (DE); Hans Henkes, Essen (DE)

(73) Assignee: DENDRON GmbH, Bochum (DE)

( * ) Notice: Subject to any disclaimer, the term of this patent is extended or adjusted under 35 U.S.C. 154(b) by 78 days.

(21) Appl. No.: 10/202,492

(22) Filed: Jul. 24, 2002

(65) Prior Publication Data

US 2004/0034378 A1  Feb. 19, 2004

(51) Int. Cl.
*A61M 29/00* (2006.01)
*A61B 18/04* (2006.01)

(52) U.S. Cl. .................. 606/198; 606/32; 606/41; 606/108

(58) Field of Classification Search ............ 606/108, 606/191, 195, 198, 200, 32, 41; 604/104, 604/106, 93.01
See application file for complete search history.

(56) References Cited

U.S. PATENT DOCUMENTS

| | | | | |
|---|---|---|---|---|
| 5,382,259 A | * | 1/1995 | Phelps et al. | 606/151 |
| 5,522,822 A | * | 6/1996 | Phelps et al. | 606/151 |
| 5,578,074 A | * | 11/1996 | Mirigian | 606/108 |
| 5,800,454 A | * | 9/1998 | Jacobsen et al. | 606/191 |
| 5,830,230 A | * | 11/1998 | Berryman et al. | 606/200 |
| 5,853,418 A | * | 12/1998 | Ken et al. | 606/191 |
| 6,093,199 A | * | 7/2000 | Brown et al. | 606/200 |
| 6,221,066 B1 | * | 4/2001 | Ferrera et al. | 606/1 |
| 6,371,972 B1 | * | 4/2002 | Wallace et al. | 606/200 |
| 6,537,293 B1 | * | 3/2003 | Berryman et al. | 606/200 |
| 6,551,340 B1 | * | 4/2003 | Konya et al. | 606/191 |
| 6,634,361 B1 | * | 10/2003 | Nikolchev et al. | 128/830 |
| 2004/0078050 A1 | | 4/2004 | Monstadt et al. | |

FOREIGN PATENT DOCUMENTS

| | | |
|---|---|---|
| EP | 0 792 623 | 9/1997 |
| WO | WO97/42881 | 11/1997 |
| WO | 99-09894 | 3/1999 |
| WO | WO00/21443 | 4/2000 |
| WO | WO01/32085 | 5/2001 |

\* cited by examiner

*Primary Examiner*—Michael J. Hayes
*Assistant Examiner*—Michael Mendoza
(74) *Attorney, Agent, or Firm*—Collard & Roe, P.C.

(57) ABSTRACT

Device for implanting occlusion spirals in body cavities or blood vessels with a catheter, an occlusion spiral that can be moved within the catheter in the longitudinal direction, and at least one securing means attached in the occlusion spiral, structured as a flexible lengthwise element, which passes through the length of the occlusion spiral at least in a partial region, which is characterized in that the securing means contains a material with shape memory properties.

19 Claims, 2 Drawing Sheets

DEVICE FOR IMPLANTING OCCLUSION SPIRALS

BACKGROUND OF THE INVENTION

The invention relates to a device for implanting occlusion spirals in body cavities or blood vessels with a catheter, an occlusion spiral that can be moved within the catheter in the longitudinal direction, and at least one securing means attached in the occlusion spiral, structured as a flexible lengthwise element, which passes through the length of the occlusion spiral at least in a partial region. The invention furthermore relates to an occlusion spiral as well as to a medical implant that is intended to be deposited in body cavities or blood vessels to be closed off.

The use of endovascular techniques for the occlusion of body cavities or blood vessels such as arteries, veins, Fallopian tubes, or vascular malformations (e.g. vascular aneurysms) is a known state of the art. In this connection, the occlusion spiral is generally introduced and deposited in the cavity to be occluded using an endovascular guide wire, by means of a catheter.

In advance of being deposited, the occlusion spirals to be implanted are guided through the vascular system using the catheter, and are advanced out of the catheter into the area to be occluded when they reach the target location. In an ideal case, this is followed by separation of the spiral. In the case of incorrect positioning or an occlusion spiral that is too large for the region to be occluded, however, the spiral has to be repositioned or completely retracted into the catheter, in order to subsequently permit correct positioning or introduction of a correctly sized occlusion spiral. Such maneuvers in the vascular system are fraught with the risk that parts of the spiral will be pulled apart under tensile or torsion stress, and thereby will be irreversibly plastically deformed, will tear, or will break, bringing with this the risk of a life-threatening embolism.

In order to minimize these risks, it is known from the reference PCT/US 98/17885 to attach a flexible securing means in the occlusion spiral. The disadvantage of this device is that the securing means, consisting of a polymer material, is not ideal with regard to bending stress or tensile strength. Therefore with this device, too, tearing of the spiral within the blood vessel system can occur if the torsion stress and/or the tensile stress is too great.

SUMMARY OF THE INVENTION

In view of the problems connected with the state of the art in depositing occlusion spirals, the task therefore exists of making available a device that allows the introduction of occlusion spirals with increased safety for the patient, as compared with known devices.

This task is accomplished, according to the invention, by means of a device of the type stated initially, in which the securing means contains a material with shape memory properties.

The term "shape memory" is sufficiently known to a person skilled in the art addressed here, and comprises both mechanically induced and thermally induced shape memory. Materials that demonstrate thermal or mechanical shape memory are understood to be materials with shape memory properties within the scope of this invention, as are materials with thermally induced and mechanically induced shape memory. In this connection, both organic materials and metal alloys with shape memory properties can be used as materials.

Such materials demonstrate the ability to change back and forth between a rather rigid and a very flexible state, depending on the temperature, whereby they also pass through transition states. Such materials can be placed under significantly greater bending stress or tensile stress than conventional materials. In this connection, the material can be bent or stretched to an extremely high degree, particularly in the flexible state, without tearing. Only when the temperature is increased does it return to its rigid state, and in the case of a prior deformation, this is accompanied by a change in shape. The temperature threshold, in each instance, can be controlled by the composition of the material, in a way generally known to a person skilled in the art.

In accordance with a preferred embodiment of the invention, the securing means consists essentially or completely of the material with shape memory properties.

The formation of the securing means with or from material with shape memory properties imparts increased bending strength and increased stability with regard to tensile and torsion stress to the device according to the invention.

In accordance with a practical embodiment, the securing means of the device according to the invention is sized to be longer than the partial region of the occlusion spiral over which it extends. The length sizing of the securing means also assures a less rigid arrangement despite stable attachment in the occlusion spiral, so that the securing means is not subject to any tensile stress in the occlusion spiral, unless there is an external effect, thereby assuring great stability and flexibility.

It is practical if a metal alloy with shape memory properties is used for the production of the securing means. These can be alloys that have the capacity of either temperature-induced or stress-induced martensite transformation. However, alloys with the capacity of undergoing both temperature-induced and stress-induced martensite transformation are preferred. Alloys containing titanium and nickel, as well as alloys based on iron or copper, are particularly suitable.

The use of such an alloy with shape memory properties demonstrates the advantage, for one thing, that metal/metal connections between the occlusion spiral and the securing means can be made more easily than those with plastic/metal connections. Alloys based on titanium and nickel furthermore demonstrate the advantage that their mechanical technology properties have been well studied.

In this connection, titanium/nickel alloys demonstrate different crystal structures, depending on the temperature: The phase present at a high temperature is referred to as austenite. Its atom arrangement is cubically surface-centered; it represents the stable phase. At a lower temperature, the atoms of such an alloy are present in a tetragonally distorted, cubically space-centered arrangement. It is referred to as martensite. The martensite phase, resulting from the temperature, is also referred to as temperature-induced martensite (TIM). In this connection, the selection of the alloy can be used to determine at what temperature a transition (transformation) from the one phase to the other will occur, where this can take place over a range of −100 to 100° C.

If no external force acts on the material during the transformation from austenite to martensite (as the result of a reduction of the temperature below a critical value), no macroscopic change in form will be observed. In the martensite state, the component can be easily deformed, and it is possible to achieve a change in shape of up to approximately 8%. As long as the material remains below the critical temperature threshold (the transformation temperature), the deformation is stable. However, if the deformed martensite is heated, the original shape is restored when the transformation temperature is exceeded. This shape memory of the temperature-induced martensite, which is controlled by different ambient temperatures, is also referred to as thermal shape memory.

Aside from this thermal shape memory, metal alloys can also possess a mechanical shape memory (superelasticity), which is based on the alloy going into a stress-induced martensite phase (SIM): In certain temperature ranges, which can be easily adjusted by a person skilled in the art by selecting a certain alloy composition, the transition to the martensite phase can also be induced mechanically, by the effect of an external force (stress-induced martensite). In this way, expansion values of up to 10% can be achieved. If the material remains at this temperature, which lies above the temperature threshold of the transformation from martensite to austenite, the material will return to the austenite phase, and reverse deformation will occur.

However, the thermal transformation from martensite to austenite takes place within a temperature range, not when a strictly limited temperature value is exceeded, so that there are transition phases in the material structure. If the effect of a mechanical stress is now eliminated at a temperature in this intermediate range, a partial, stress-induced reverse transformation to austenite, and therefore partial reverse deformation, will come about. Only when the temperature increases does a complete transformation to the austenite phase occur. In this case, a combination of stress-induced and temperature-induced phase transformation is present.

Because of the particularly high tensile stress that such metal alloys can withstand in the martensite state (i.e. in the temperature-induced and/or stress-induced martensite state), the material used for the production of the securing means is preferably selected in such a way that the securing means is present in the catheter in the form of stress-induced and/or temperature-induced martensite, and is transformed, at least partially, to the austenite phase upon introduction into the blood vessel system or into the aneurysm to be occluded, as a result of the elimination of the force exerted by the catheter and/or the increase in ambient temperature, and thereby fills the aneurysm in stable manner. In this connection, depending on the situation, it can be practical to use an alloy that passes through a purely stress-induced or purely temperature-induced transformation, or a mixed transformation, when it is pushed out of the microcatheter.

Alloys with a transformation temperature between +35° C. and +38° C. are particularly suitable for taking advantage of thermally-induced shape memory in the body. Alloys with a transformation temperature between −15° C. and +38° C. and, in particular, −15° C. and +20° C., are particularly suitable for taking advantage of stress-induced shape memory in the body. However, the transformation temperatures particularly suitable for inducing shape memory effects in the body are sufficiently known to a person skilled in the art.

In accordance with a practical embodiment, the securing means is structured as a metal wire. This embodiment has the advantage that wire is very inexpensive and can be easily attached in the occlusion spiral with its two ends.

An embodiment in which the securing means is preformed is particularly practical. Here, preforming of the securing means into the shape of a spring or spiral, and preferably into a spiral spring or helical spiral, is particularly practical. This embodiment demonstrates particularly tensile strength, since the securing means structured as a spring or spiral is first deformed elastically, without any irreversible expansion taking place. When the limit of elastic deformability of the spring or spiral is exceeded, the great flexibility of the material with thermal shape memory and/or superelastic properties then goes into effect, so that double security to prevent tearing of the occlusion spiral is present.

Since the distal tip of the occlusion spiral is subject to particularly great stress during introduction into the blood vessel, it is practical if the securing means extends to the distal tip segment and is rigidly, in other words non-releasably connected with it. From the tip segment, it can extend over a partial region, or over the entire length of the occlusion spiral in the proximal direction, in this connection.

Particularly in the case were the securing means is longer than the region of the occlusion spiral over which it extends, it is possible, without any loss in mobility and flexibility, for the securing means to extend completely from the proximal end to the distal end of the occlusion spiral, even if the occlusion spiral has a great length of several 100 mm. This allows securing of the entire occlusion spiral against tearing, without any loss in control and mobility of same within the catheter or blood vessel.

In accordance with another practical embodiment of the device according to the invention, the wire that forms the occlusion spiral becomes thinner, and/or the securing means becomes thinner, towards its proximal and/or distal end. If the securing means becomes thinner, an embodiment of the device according to the invention in which the securing means is structured as a wire is particularly suitable.

Thinning towards the proximal direction takes into account the fact that when the last coils of the occlusion spiral are introduced into an aneurysm, the aneurysm is already under great stress, resulting from the first lengths of the occlusion spiral or spirals. Experiments by the inventors have shown that thinning of the proximal regions, in other words the regions introduced last, X minimizes the risk that introduction of these last segments is accompanied by a wall rupture of the aneurysm. Thinning of the securing means or wire in the distal direction (in other words the segment introduced into the aneurysm first) allows a minimally traumatic method of procedure, because in this case the tip of the occlusion spiral is particularly flexible in this case. For the size of the wire, diameters between 0.02 and 0.2 and, in particular, between 0.03 and 0.1 mm, are particularly suitable. In order to still demonstrate sufficient tensile strength, thinning should result in at most a diameter of 0.01 mm, but preferably not less than 0.03 mm.

The securing means can fundamentally be connected with the occlusion spiral directly, but also indirectly. In this connection, it is practical if the securing means is connected with the occlusion spiral indirectly, by way of connection means. An embodiment in which microspirals that are rigidly connected with the securing means and the occlusion spiral are used as connection means is particularly practical. This embodiment is particularly inexpensive, since conventional occlusion spirals can be used for its production, with the combination of securing means and at least two microspirals attached at the ends of the securing means being inserted and connected with the occlusion spiral using conventional methods.

In this connection, measures that are sufficiently known to a person skilled in the art, such as welding, soldering, gluing, or mechanical (i.e. non-positive-lock and/or positive-lock) joining methods are suitable for connecting the microspirals with the occlusion spiral and with the securing means, respectively.

When using organic materials with shape memory properties for producing the securing means, a mechanical connection or gluing is a particular possibility. When using metal alloys with shape memory properties, on the other hand, basically all the connection methods listed above are suitable. In this connection, mechanical joining methods (i.e. non-positive lock and/or positive lock connections) are particularly preferred.

In accordance with a preferred embodiment of the invention, the microspirals and the occlusion spiral are made from the same material. Platinum and platinum alloys (particularly Pt—Ir alloys) are particularly suitable for forming the microspirals and the occlusion spiral; these are materials that are used for the production of occlusion spirals, in many cases in the production of occlusion spirals because of their low level of traumatization during introduction into the vascular system. In addition, in this embodiment the microspirals can be connected with the occlusion spiral in particularly stable manner, by means of welding.

In this connection, it is particularly practical if the securing means consists of an alloy containing titanium and nickel, since the behavior of such alloys is well known in the state of the art.

In accordance with another preferred embodiment, the occlusion spiral is structured as a microspiral. It is particularly practical if it is additionally preformed to produce an overriding structure that it takes on after ejection from the catheter, in the aneurysm. This embodiment is particularly well suited for thrombotization of aneurysms.

Furthermore, it can be practical if the securing means itself is preformed to produce a two-dimensional or three-dimensional design, preferably also to form helical coils or a basket-like design. In this embodiment, the securing means supports the assumption of a two-dimensional or three-dimensional design by the occlusion spiral. In this connection, it can be sufficient, for the purpose of forming such a design, if only the securing means, but not the occlusion spiral, is preformed, if the force exerted by the securing means until the preformed structure is reached is sufficiently great so that the occlusion spiral is also forced into the shape predetermined by the securing means.

In this connection, it can be particularly practical if the securing means is structured as a spring or spiral, and particularly as a spiral spring or a helical spiral, which is deformed to produce an overriding two-dimensional or three-dimensional design.

In accordance with a particularly preferred embodiment of the device according to the invention, the securing means is preformed and is preferably present in the catheter at least partially in a state of stress-induced martensite. When it is pushed out of the catheter, it then takes on the preformed design, because of the elimination of the mechanical stress and/or the increasing temperature in the bloodstream, and forms a three-dimensional helix or a basket structure, for example.

In another practical embodiment, the occlusion spiral has one or more electrolytically corrodable locations arranged at a distance from one another, and can therefore break up into one or more lengths, which can be made variable in size, by means of electrolytic corrosion, in connection with an electrically insulating catheter and a voltage source as well as a cathode, in contact with a body fluid. The electrolytic break-up of occlusion spirals is sufficiently known to a person skilled in the art, and demonstrates many advantages with regard to practicability, safety, and cost-effectiveness as compared with other measures for breaking up occlusion spirals that are known in the state of the art.

It is particularly practical, in this connection, if the occlusion spiral has several electrolytically corrodable locations, where a securing means is arranged in each of the segments located between these locations, preferably extending from the one end to the other of each segment. This embodiment makes it possible to deposit lengths of occlusion spirals that can be varied in size, where at the same time, a maximum degree of security against tearing of the occlusion spiral is assured by securing each individual segment arranged between the electrolytically corrodable locations.

In accordance with a particularly practical embodiment, each segment of the occlusion spiral is formed by at least two, preferably at least three microspirals with different diameters, inserted into one another, where the spiral adjacent to the electrolytically corrodable location at the proximal or distal end, in each instance, is rigidly connected with this location. This embodiment, made up of individual components, is particularly inexpensive to produce. In this connection, the securing means is either affixed to one of the microspirals, or is attached to them indirectly, by way of the connection means (which themselves are structured as microspirals, for example) that are rigidly connected with them.

Furthermore, an embodiment in which an insertion aid structured as a guide wire follows the occlusion spiral in the proximal direction is practical.

The device according to the invention is preferably intended for use in veterinary medicine or human medicine procedures, particularly the endovascular treatment of intracranial aneurysms and acquired or congenital arterio-venous vascular malformations and/or fistulas, or tumor embolization by means of thrombotization.

The invention furthermore relates to an occlusion spiral as described above, as well as to a medical implant that comprises a partial region of an occlusion spiral that contains at least one securing means and can be deposited, according to the above description.

BRIEF DESCRIPTION OF THE DRAWINGS

The invention will be explained in greater detail below, using the exemplary embodiments illustrated in the drawings. These show.

DETAILED DESCRIPTION OF THE INVENTION

Figure 1:
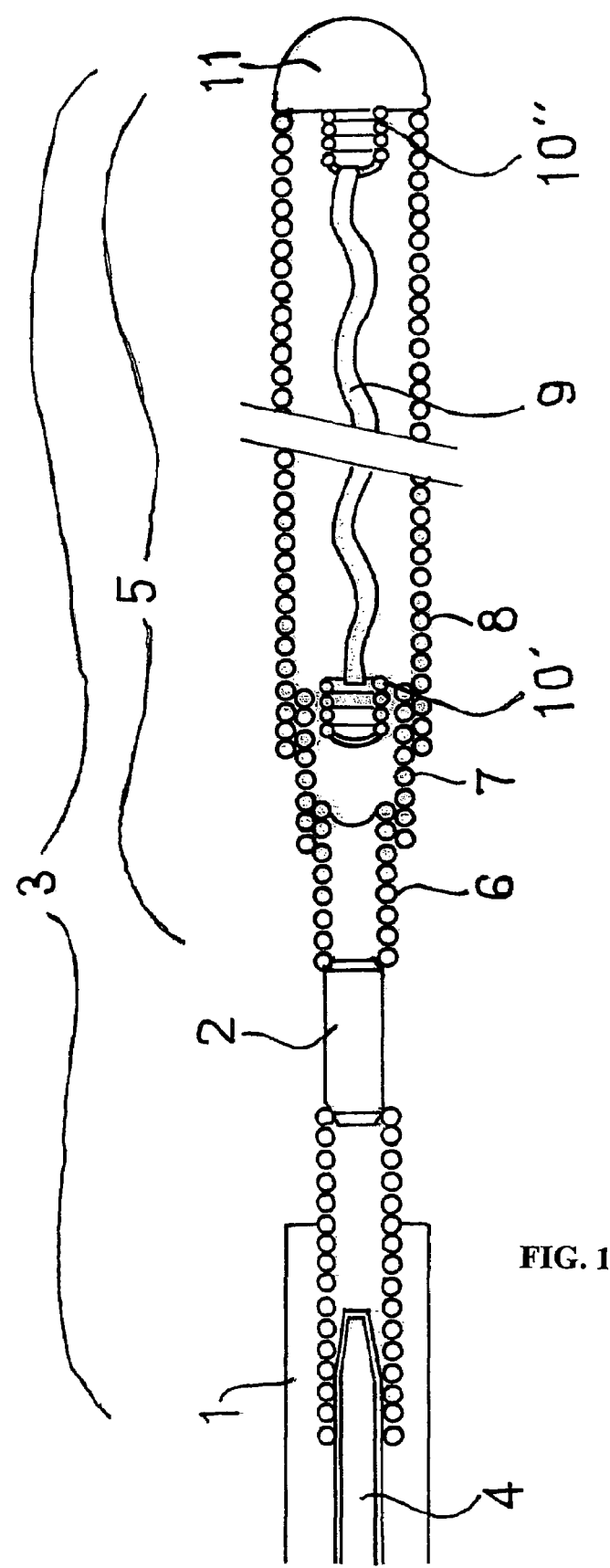
FIG. 1 a longitudinal cross-section through a device according to the invention, in a side view and magnified several times.

In FIG. 1, 1 refers to an electrically insulating catheter, particularly a flexibly structured microcatheter. An occlusion spiral 3 structured as a microspiral, made of a platinum/iridium alloy, provided with electrolytically corrodable locations 2 made of stainless steel, is pushed into the blood vessel system, out of the microcatheter 1, using the guide wire 4 that is attached to the occlusion spiral 3 using welding technology.

Since the connection between the guide wire 4 and the microspiral 3, which is produced by welding different materials, is not intended for electrolytic separation of the microspiral 3, it is structured to be particularly stable. The use of non-rusting stainless steel and a platinum alloy, respectively, for forming the guide wire, on the one hand, and the occlusion spiral, on the other hand, is particularly advantageous in this connection, since the nickel contained in the steel makes a very smooth and stable join with the platinum during welding.

The occlusion spiral 3 has a segment 5 that can be separated electrolytically and is connected with the electrolytically corrodable location 2 arranged proximal to it by means of welding of different materials. At its proximal end, the segment has a first microspiral 6 with a small diameter, which is connected at its proximal end with the electrolytically corrodable location 2 that follows it, by means of welding technology, and at its distal end with another microspiral 7 with a medium diameter. This microspiral 7 with a medium diameter partially lies around the first microspiral 6 and is also connected with it by means of welding technology. Finally, the third microspiral 8, with the longest size and the greatest diameter, and with a securing wire 9 made of a nickel/titanium allow running through it, lies around the second microspiral 7.

The wire 9 is attached at both of its ends with a connection means 10 consisting of a platinum/iridium alloy, by means of welding of different materials, in each instance. The two connection means affixed at the ends of the securing wire 9 are also structured as microspirals 10'/10", which are rigidly welded to the proximal and distal second microspiral 7, in each instance, of each segment. The securing wire is sized in such a way that its length is greater than the length of the segment 5 through which it passes. On the basis of this structure, the occlusion spiral 3, which is structured as a microspiral, is particularly flexible and, at the same time, resistant to bending stress and torsion stress.

The wire that forms the securing means 9 has an average diameter of approximately 0.03 to 0.05 mm, and becomes thinner at its proximal end (i.e. towards the guide wire), so that the regions of the occlusion spiral that are pushed into an aneurysm first, in each instance, form stable structures that are only filled out by the subsequent, proximal regions, without these proximal regions exerting an overly great force on the aneurysm, which is already in the filling process. This embodiment minimizes the risk of wall rupture by the proximal regions of the occlusion spiral 3 that are introduced into the aneurysm last. The distal tip of the occlusion spiral 11 is rounded off, in order to minimize the risk of traumatization of the aneurysm. On the inside, the tip 11 is rigidly connected with the distal microspiral 10, which serves as a connecting means, by means of welding technology, so that even if the tip 11 and adjacent regions of the occlusion spiral 3 were to break off or tear off from the proximal remainder of the occlusion spiral 3, the tip 11 would not get into the bloodstream and possibly cause embolisms there.

Figure 2:
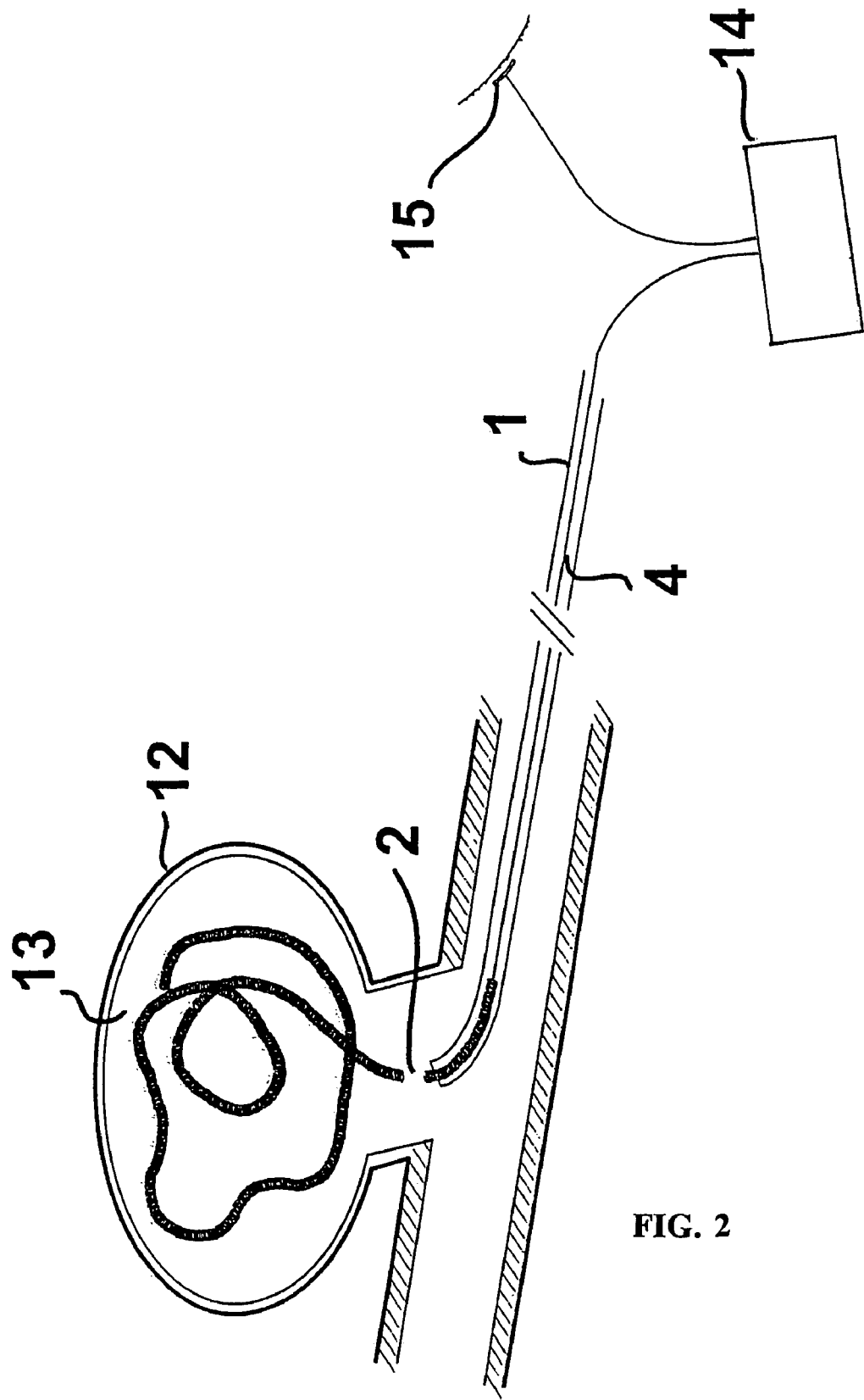
FIG. 2 a vertical view of an occlusion spiral positioned in a berry aneurysm, with the related device, magnified several times.

FIG. 2 shows a vertical view of an occlusion spiral 3 positioned in a berry aneurysm 12. Introduction of the microspiral 3, which forms secondary coils 13 after leaving the microcatheter 1, into the aneurysm 12 takes place by means of the shift in the guide aid 4 that takes place in the distal direction, in the longitudinal axis of the microcatheter 1. The formation of the secondary coils 13 is assured by the securing wire 9, which here contributes to the shaping of the occlusion spiral 3, at the same time. This wire, which consists of a titanium/nickel alloy, is structured as a spring, which is additionally preformed to produce an overriding two-dimensional or three-dimensional design.

When the occlusion spiral is placed in the catheter, stress-induced martensite transformation takes place, since the securing wire can no longer take on the overriding design. When the occlusion spiral is pushed out of the microcatheter, an elimination of the mechanical stress occurs, and the ambient temperature increases slightly, to body temperature. As a result of these influences, the securing wire undergoes a transformation, partly stress-induced and partly temperature-induced, and goes over into the austenite phase. Upon introduction of the occlusion spiral into the bloodstream, a combination of superelastic and temperature-induced transformation of the securing wire therefore takes place. In this connection, the microstructure of the material of the securing wire undergoes a transformation, while the securing wire undergoes only a change in shape. The securing wire resumes the overriding design. The change in shape of the securing wire has the result that the occlusion spiral takes on a predefined two-dimensional or three-dimensional design, under the effect of the force of the securing wire.

Because the guide wire 4 and the occlusion spiral 3 can shift longitudinally in the microcatheter 1, a length of the occlusion spiral 3 individually adapted to the volume of the cavity to be filled, in each instance, is introduced into this cavity. Subsequently, a voltage is applied over a period of 0.1 to 20 min, using the voltage source 14, the cathode 15 positioned on the surface of the body, and the occlusion spiral 3 positioned in the aneurysm 12 to be occluded, which serves as the anode. In this way, electrolytic separation of the part of the occlusion spiral that is located in the blood is triggered at the electrolytically corrodable location 2 that is closest to the distal catheter end. FIG. 2 shows an occlusion spiral whose electrolytically corrodable location 2 located closest to the distal end of the microcatheter 1 was already electrolytically corroded.

The invention claimed is:

1. An assembly for implanting an occlusion coil in a body cavity or a blood vessel via a catheter comprising:
   (a) an occlusion coil comprising at least one electrolytically corrodable location;
   (b) at least one longitudinally flexible safety element extending into at least a part of a length of the occlusion coil, said safety element comprising a material with shape memory; and
   (c) a plurality of microcoils rigidly connected to said safety element and the occlusion coil for securing said safety element to the occlusion coil;
   wherein the safety element is sized to be longer than the part of the occlusion coil over which it extends so that the safety element is not subject to any tensile stress in the absence of an external force; and
   wherein a first microcoil connects the distal end of said electrolytically corrodable location with a second microcoil and the second microcoil is connected with the occlusion coil.

2. The assembly according to claim 1, wherein the safety element essentially consists of a material with shape memory.

3. The assembly according to claim 1, wherein the material is a metal alloy with the capacity of undergoing temperature-induced martensite transformation.

4. The assembly according to claim 3, wherein the metal alloy is an alloy containing titanium and nickel, an iron-based alloy or a copper-based alloy.

5. The assembly according to claim 3, wherein the safety element is a wire with shape memory comprising a metal alloy with the capacity of undergoing stress-induced martensite transformation.

6. The assembly according to claim 3, wherein the metal alloy demonstrates the capacity of undergoing stress-induced martensite transformation.

7. The assembly according to claim 1, wherein the occlusion coil is structured as a microcoil.

8. The assembly according to claim 1, wherein the safety element is preformed.

9. The assembly according to claim 8, wherein the safety element is preformed to a helical coil or a coil spring.

10. The assembly according to claim 8, wherein the preformed safety element has a capacity to pass through temperature-induced martensite transformation at body temperature.

11. The assembly according to claim 1, wherein the occlusion coil is preformed to produce secondary coils or a cage-shaped design.

12. The assembly according to claim 1, wherein an insertion aid structured as a guide wire follows in the proximal direction.

13. The assembly according to claim 1, wherein the safety element extends to a distal tip segment of the occlusion coil and has one end rigidly connected with the distal tip segment via one of said microcoils.

14. The assembly according to claim 1, wherein the connection between the microcoils and the occlusion coil and/or the safety element is brought about by welding, soldering, gluing, or mechanical connections.

15. The assembly according to claim 1, wherein the microcoils are produced from the same material as the occlusion coil.

16. The assembly according to claim 15, wherein the material forming the microcoils and the occlusion coil is platinum or a platinum alloy.

17. An assembly for implanting an occlusion coil in an aneurysm or a blood vessel via a catheter comprising:
   (a) an occlusion coil;
   (b) an electrically insulating catheter; and
   (c) at least one longitudinally flexible preformed safety element extending into at least a part of a length of the occlusion coil, said safety element comprising a material with shape memory in a martensite phase, said material undergoing at least partial stress-induced martensite transformation when placed in the blood vessel or the aneurysm to assume a stable phase shape; wherein the occlusion coil has several electrolytically corrodable locations, where a safety element is arranged in each segment of the occlusion coil located between these locations; and
   wherein each segment of the occlusion coil is formed by at least two microcoils with different diameters, inserted one inside the other, where the coil that is adjacent to the electrolytically corrodable location, proximally or distally, in each instance, is rigidly connected with the electrolyically corrodable location.

18. An assembly for implanting an occlusion coil in a body cavity or a blood vessel via a catheter comprising:
   (a) an electrically insulating catheter;
   (b) an occlusion coil comprising one or more spatially separated electrolytically corrodable locations and at least one segment;
   (c) at least one longitudinally flexible safety element extending into at least a part of a length of the occlusion coil, said safety element comprising a material with shape memory;
   (d) a voltage source; and
   (e) a cathode;
   wherein one or more variably sized lengths of said occlusion coils are separable by electrolysis upon contact with body fluid; and
   wherein the safety element is sized to be longer than the part of the occlusion coil over which it extends; and
   wherein each segment of the occlusion coil is formed by at least two microcoils with different diameters, inserted one inside the other, where the coil that is adjacent to the electrolytically corrodable location, proximally or distally, in each instance, is rigidly connected with the electrolyically corrodable location.

19. A medical implant comprising an occlusion coil having at least one depositable partial region, at least one longitudinally flexible safety element extending into at least a part of a length of the occlusion coil, said safety element comprising a material with shape memory, and a plurality of microcoils rigidly connected to said safety element and the occlusion coil for securing said safety element to the occlusion coil;
   wherein the safety element is sized to be longer than the part of the occlusion coil over which it extends;
   wherein said occlusion coil comprises at least one electrolytically corrodable location and at least one segment; and
   wherein each segment of the occlusion coil is formed by at least two microcoils with different diameters, inserted one inside the other, where the coil that is adjacent to the electrolytically corrodable location, proximally or distally, in each instance, is rigidly connected with the electrolyically corrodable location.

* * * * *

UNITED STATES PATENT AND TRADEMARK OFFICE
CERTIFICATE OF CORRECTION

PATENT NO. : 7,238,194 B2 Page 1 of 1
APPLICATION NO. : 10/202492
DATED : July 3, 2007
INVENTOR(S) : Hermann Monstadt and Hans Henke It is certified that error appears in the above-identified patent and that said Letters Patent is hereby corrected as shown below:

<u>TITLE PAGE; ITEM (30); ON THE FRONT OF THE PATENT:</u>

Please add the related Foreign Applications as claimed by applicant as follows:

--Foreign Applications--
--GERMANY 101 18 017.9 04/10/2001--

Signed and Sealed this

Sixteenth Day of September, 2008

JON W. DUDAS
*Director of the United States Patent and Trademark Office*